United States Patent
Lee

(10) Patent No.: US 6,336,739 B1
(45) Date of Patent: Jan. 8, 2002

(54) AIR BATH DISSOLUTION TESTER

(76) Inventor: Luke Lee, 19 C Schoolhouse Rd., Somerset, NJ (US) 08873

( * ) Notice: Subject to any disclaimer, the term of this patent is extended or adjusted under 35 U.S.C. 154(b) by 0 days.

(21) Appl. No.: 09/796,370

(22) Filed: Mar. 2, 2001

(51) Int. Cl.⁷ .......................... B01F 1/00; G01N 13/00; B01L 7/00
(52) U.S. Cl. ...................... 366/143; 366/145; 366/147; 366/149; 73/866; 73/61.43; 422/68.1
(58) Field of Search ................................ 366/144, 146, 366/234, 279, 343, 149, 147, 145, 143, 142; 73/866, 54.28, 61.71, 61.43, 864.81, 864.82, 864.83; 422/68.1

(56) References Cited

U.S. PATENT DOCUMENTS

| | | | |
|---|---|---|---|
| 364,566 A | * 6/1887 | Avers et al. | |
| 1,689,103 A | * 10/1928 | Bendixen | |
| 1,984,047 A | * 12/1934 | Thieme | |
| 2,104,456 A | * 1/1938 | Friedman | |
| 2,141,713 A | * 12/1938 | Hensler et al. | |
| 3,039,859 A | * 6/1962 | Kurz | 366/147 |
| 3,109,913 A | * 11/1963 | Galajda, Jr. | 366/146 |
| 3,168,431 A | * 2/1965 | Spielvogel | 366/147 |
| 3,329,409 A | * 7/1967 | Raleigh | 366/146 |
| 3,467,500 A | * 9/1969 | Wilkinson et al. | 366/140 |
| 3,572,648 A | * 3/1971 | Hanson | 366/349 |
| 3,618,395 A | * 11/1971 | Melliger | |
| 3,742,190 A | * 6/1973 | Giani et al. | |
| 3,791,221 A | * 2/1974 | Kirschner et al. | 73/866 |
| 3,791,222 A | * 2/1974 | Goodhart et al. | 73/866 |
| 3,802,272 A | 4/1974 | Bischoff et al. | 366/142 |
| 3,893,811 A | * 7/1975 | Good et al. | 366/147 |
| 4,335,438 A | * 6/1982 | Smolen | |
| 4,464,340 A | * 8/1984 | Lennox, Jr. et al. | 422/103 |
| 4,578,244 A | * 3/1986 | Cosgrove, Jr. et al. | 422/81 |
| 4,593,563 A | * 6/1986 | Laine et al. | |
| 4,678,639 A | * 7/1987 | Dong et al. | 422/81 |
| 4,681,858 A | * 7/1987 | Chaudhari et al. | 73/866 |
| 4,708,023 A | * 11/1987 | Schneider et al. | |
| 4,725,149 A | * 2/1988 | Kawakami et al. | 366/146 |
| 4,751,052 A | * 6/1988 | Schwartz et al. | |
| 4,792,434 A | * 12/1988 | Metzger et al. | |
| 4,856,909 A | 8/1989 | Metha et al. | 366/208 |
| 4,858,155 A | * 8/1989 | Okawa et al. | 364/557 |
| 4,879,917 A | * 11/1989 | Eppelmann et al. | 73/866 |
| 4,924,716 A | * 5/1990 | Schneider | 73/866 |
| 4,964,310 A | * 10/1990 | Schneider | 73/866 |
| 5,011,662 A | * 4/1991 | Noormohammadi et al. | 422/68.1 |
| 5,055,273 A | 10/1991 | Wilhelm et al. | |
| 5,076,107 A | * 12/1991 | Timmermans et al. | 73/866 |
| 5,142,920 A | * 9/1992 | Bart et al. | 73/866 |
| 5,174,508 A | * 12/1992 | Martin | 241/21 |
| 5,285,681 A | * 2/1994 | Binder et al. | |
| 5,380,485 A | * 1/1995 | Takahashi et al. | |
| 5,403,090 A | * 4/1995 | Hover et al. | 366/142 |
| 5,412,979 A | 5/1995 | Fassihi | |
| 5,540,496 A | 7/1996 | Beckett et al. | |
| 5,577,837 A | * 11/1996 | Martin et al. | 366/147 |

(List continued on next page.)

Primary Examiner—Tony G. Soohoo
(74) Attorney, Agent, or Firm—Richard C. Litman

(57) ABSTRACT

Air bath dissolution tester has a heating element within the USP specification dissolution test stirring shaft, easily attachable to a basket-type (USP) method I, or paddle (USP method II). This allows direct heat transfer to the test solution in the vessel, reducing heat up time. Temperature in the vessel is controlled by a controller responsive to test vessel temperature sensor. Temperature data is obtained during the test. The test vessel is located in a warm air chamber to prevent heat loss. The air chamber and test vessel are transparent, allowing the operator to determine the progress of the test. No water bath is required. The heated SS shaft promotes test solution degassing by direct heating and high-speed stirring during heat up, thus eliminating a separate step.

20 Claims, 4 Drawing Sheets

U.S. PATENT DOCUMENTS

| | | | |
|---|---|---|---|
| 5,589,649 A | 12/1996 | Brinker et al. | 73/866 |
| 5,639,974 A * | 6/1997 | Hanson et al. | 73/866 |
| 5,682,001 A * | 10/1997 | Hanson et al. | 73/866 |
| 5,796,016 A * | 8/1998 | Muller | 73/866 |
| 5,807,115 A * | 9/1998 | Hu | 434/272 |
| 5,816,701 A | 10/1998 | Martin et al. | 366/142 |
| 5,827,984 A * | 10/1998 | Sinnreich et al. | 73/866 |
| 6,060,024 A * | 5/2000 | Hutchins et al. | 422/81 |
| 6,170,980 B1 * | 1/2001 | Martin | 73/866 |
| 6,174,497 B1 * | 1/2001 | Roinestad et al. | 73/866 |

* cited by examiner

AIR BATH DISSOLUTION TESTER

BACKGROUND OF THE INVENTION

1. Field of the Invention

The present invention relates to dissolution testers. More particularly, the present invention relates to apparatus measuring the rate of dissolution of materials such as pharmaceuticals, particularly those in pill or capsule form.

2. Description of the Related Art

Dissolution testing is used to determine the rate of dissolution of pharmaceuticals in dosage forms in specific test solutions to simulate digestion in a human or animal. The requirement for such dissolution testing apparatus is provided in United Sates Pharmacopoeia(USP), Edition XXII, Section 711, Dissolution(1990).

Conventional dissolution testers have one or more test vessels in the same apparatus where the test solution may be placed. For each test vessel, there is a stirring device. As described in USP method I, a basket-type stirring element consisting of stainless steel(SS) shaft with a cylindrical basket at its lower end is specified. As described as USP method II, a paddle-type stirring element consisting of SS shaft with an SS blade at its lower end is specified.

As per USP requirement, the test solution placed in the dissolution vessel must be maintained at a constant 37° C. For the conventional dissolution tester, the dissolution vessel is placed in a temperature controlled water bath. Heat is transferred to the vessel solution by means of the water bath. This conventional process is time-consuming; it takes more than an hour to heat the solution to the desired temperature. Water baths also have inherent problems such as leakage, evaporation, and algae growth. A water bath requires a considerable amount of water which requires heating. This process leads to excessive electric power consumption. In addition, water bath apparatus requires draining and cleaning. After cleaning, the bath must be refilled and heated to the desired temperature, a time-consuming task.

As per USP dissolution testing procedure, the test vessel solution temperature must be measured before the test is initiated. It is not permitted to put a temperature thermometer into the test vessels during the dissolution test. For conventional dissolution testers, the dissolution-testing operator measures only the water bath temperature during the test, itself. As a result, there are no direct temperature measurements of test vessels during the testing process, thus there is no true temperature data.

As per USP specification, all thee solution in the test vessel must be degassed. In conventional dissolution testing apparatus the operator must degas the test solution before it is poured into the dissolution vessel. The degassing is performed by heating, stirring or by vacuum techniques. This is an additional task which must be carried out by the operator.

The problems, then, associated with a conventional dissolution may be summarized as follows: (1) non direct heat—it takes too long to heat the test vessel solution to desired temperature; (2) energy waste—substantial energy is required in heating extensive amounts of water solely for heat transfer; (3) time consuming—it takes substantial time to clean the bath, maintain clean water at the desired temperature, avoid leakage, compensate for evaporation, and perform required maintenance; (4) lack of direct temperature data—there is no means to measure the actual test vessel temperature during the dissolution testing procedure (temperature is critical in dosage dissolution rates); (5) degassing required—the operator must degas the test solution.

It is desirable, then, to have an improved dissolution tester, exhibiting: (1) a faster heat up time, thus increasing productivity; (2) elimination of a water bath for solution heating; (3) providing direct test vessel temperature data throughout the test; and (4) elimination of the solution degassing step.

U.S. Pat. No. 5,589,649, issued Dec. 31, 1996, to Brinker et al., describes a rotating paddle type dissolution testing apparatus featuring a heater and temperature sensor for each test vessel. The heating elements are wrapped around the outside of the test vessels. Each stirring element has a hollow shaft in which the temperature sensors are placed. The '649 patent would necessarily experience difficulty in maintaining a uniform temperature using direct heating elements due to inherent difficulties in mechanical heat transfer and the maintenance of the heating elements.

U.S. Pat. No. 5,540,496, issued Jul. 30, 1996, to Beckett et al. describes a dissolution test flow cell featuring a heater-circulator 55 in FIG. 1, thereof.

U.S. Pat. No. 5,055,273, issued Oct. 8, 1991, to Wilhelm et al. describes a hollow, heatable stirrer for use with viscous liquids in a reactor or mixer.

U.S. Pat. No. 3,802,272, issued Apr. 9, 1974, to Bischoff et al., describes a dissolution test apparatus employing a rotating basket type tablet holder.

U.S. Pat. No. 4,856,909, issued Aug. 15, 1989, to Mehta et al. describes a basket type dissolution tester featuring a solvent-containing glass beaker heated by a thermostatically-controlled bath for holding the temperature of the solvent at about 37° C.

U.S. Pat. No. 5,816,701, issued Oct. 6, 1998, to Martin et al. describes a dissolution tester featuring standard beakers, each surrounded by an aluminum platen containing heating elements, and featuring a thermistor for measuring the platen temperature, the heating elements being controlled by means of a computer responsive to the thermistor. The solution in the beaker may then be controlled at the desired temperature for the dissolution test. The '701 patent platen would appear to take a substantial length of time to reach a uniform desired temperature.

U.S. Pat. No. 5,412,979, issued May 9, 1995, describes a typical paddle type dissolution vessel having an internal solution and a liquid heating bath.

None of the above inventions and patents, taken either singularly or in combination, is seen to describe the instant invention as claimed. Thus, an air bath dissolution tester solving the aforementioned problems is desired.

SUMMARY OF THE INVENTION

The present air bath dissolution tester solves the above-mentioned problems. It provides a heating element within the USP specification dissolution test stirring shaft, the shaft being configured to be easily attachable to a basket-type (USP) method I or paddle (USP method II). This allows direct heat transfer to the test solution in the vessel directly, reducing the time required to heat the test vessel solution to the desired level. Temperature in the vessel is controlled by placing a surface sensor on the outside wall of the test vessel, preferably near its base, allowing temperature data to be displayed and recorded during the test and serving as a sensor for an automatic control system which maintains the test vessel temperature during dissolution testing. The test vessel is located in an air chamber to prevent heat loss. The air chamber functions a heat jacket, keeping heat in the test vessel and separate from cool environmental air. The air chamber is transparent, so the operator can see through the air chamber wall to check the motion of the stirring device and the dissolving dosage during the dissolution test. This allows for the total elimination of the requirement of a water bath. The heating element in the SS shaft promotes test solution degassing by direct heating and high-speed stirring while the test solution is being heated to operating temperature, thus eliminating a separate step.

Accordingly, it is a principal object of the invention to provide a dissolution tester apparatus having rapid heating to operating temperature, resulting in increased productivity.

It is another object of the invention to provide a dissolution tester apparatus which requires no water bath.

It is a further object of the invention to provide a dissolution tester apparatus which allows the direct measure and recording of the test vessel solution temperature.

Still another object of the invention is to provide for direct heating of the test vessel solution and the automatic control of the solution during a dissolution test.

Yet another object of the invention is to provide for degassing of the test vessel solution during the heating period, thus eliminating a separate step.

Still another object of the invention is to provide an apparatus as above which meets the requirements for dissolution testing apparatus as provided for in the USP.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present inventive air bath dissolution tester solves the above-mentioned problems. It provides a heating element within the USP specification dissolution test stirring shaft, the shaft being configured to be easily attachable to a basket-type (USP) method I or paddle (USP method II). This allows direct heat transfer to the test solution in the vessel directly, reducing the time required to heat the test vessel solution to the desired level. Temperature in the vessel is controlled by placing a surface sensor on the outside wall of the test vessel, preferably near its base, allowing temperature data to be displayed and recorded during the test and serving as a sensor for an automatic control system which maintains the test vessel temperature during dissolution testing. The test vessel is located in an air chamber to prevent heat loss. The air chamber functions a heat jacket, keeping heat in the test vessel and separate from cool environmental air. The air chamber is transparent, so the operator can see through the air chamber wall to check the motion of the stirring device and the dissolving dosage during the dissolution test. This allows for the total elimination of the requirement of a water bath. The heating element in the SS shaft promotes test solution degassing by direct heating and high-speed stirring while the test solution is being heated to operating temperature, thus eliminating a separate step.

Figure 1:
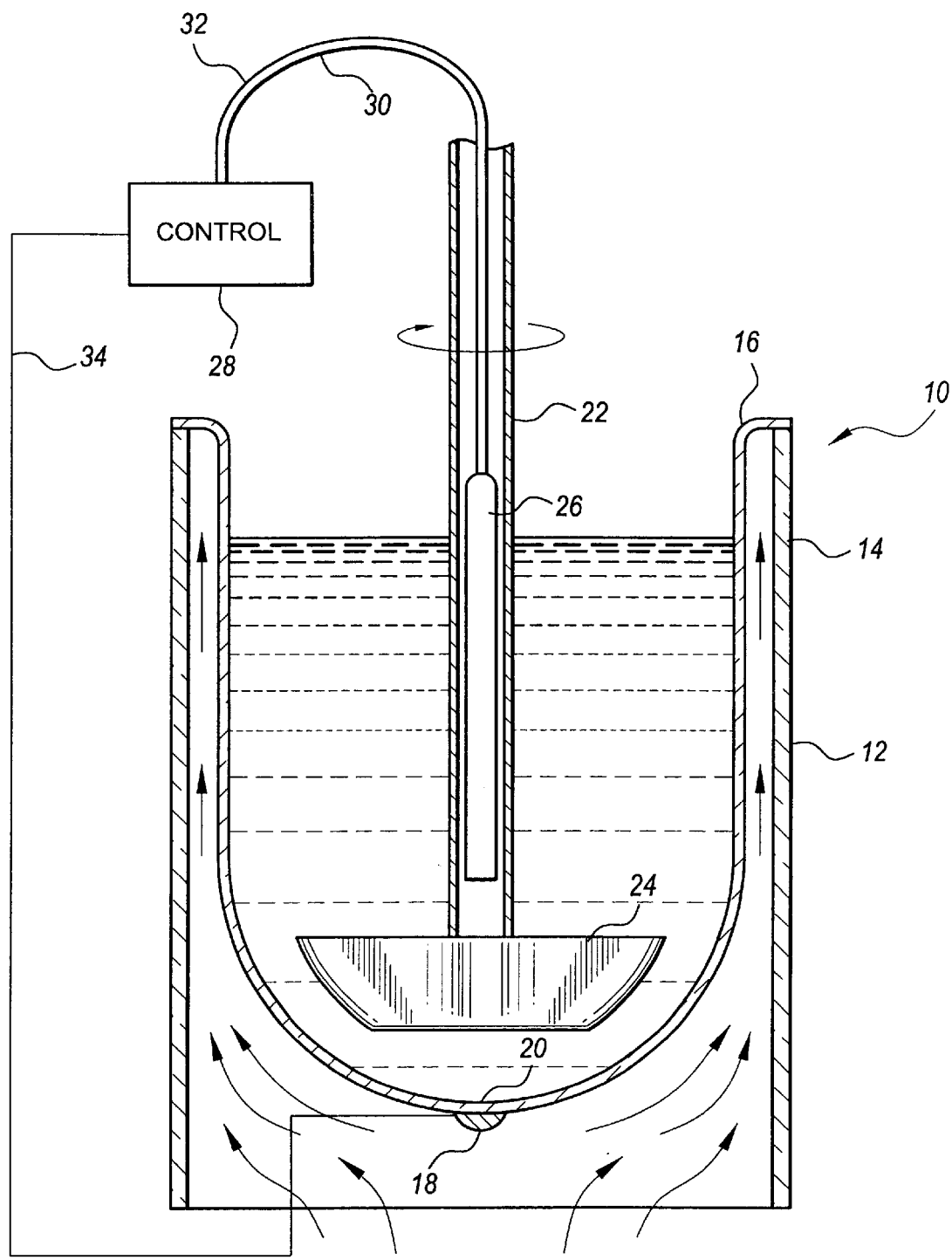
FIG. 1 is a diagrammatic, elevation view of the dissolution tester of the present invention.

Referring to FIG. 1, there is illustrated the dissolution tester system of the present invention 10 which includes dissolution tester 12 having cylindrical warm air bath or jacket 14 and solution tester solution vessel 16. Solution vessel 16 is generally cylindrical, having a rounded bottom and an upper outwardly extending lip which is so configured as to rest on the upper end of air jacket 14. A temperature sensor 18, such as a thermocouple, is attached to the bottom end 20 of solution vessel 16 by any appropriate means, such as a rubber adhesive patch, so as to insure intimate contact between the outer surface of vessel 16 and temperature sensor 18. Stainless steel rotatable shaft 22 is axially located within vessel 16 and supports paddle agitator 24 mounted at its lower end. Electrical heating element 26 is located within a hollow portion of the rotatable shaft 22 and is provided with electrical power by electrical conduits 30 and 32 controlled by control 28. Control 28 activates heating element 26 in response to a signal from temperature sensor 18 through electrical conduit 34 so as to allow the heating of test solution to 37° C. and then maintain that temperature throughout the dissolution test.

Figure 2:
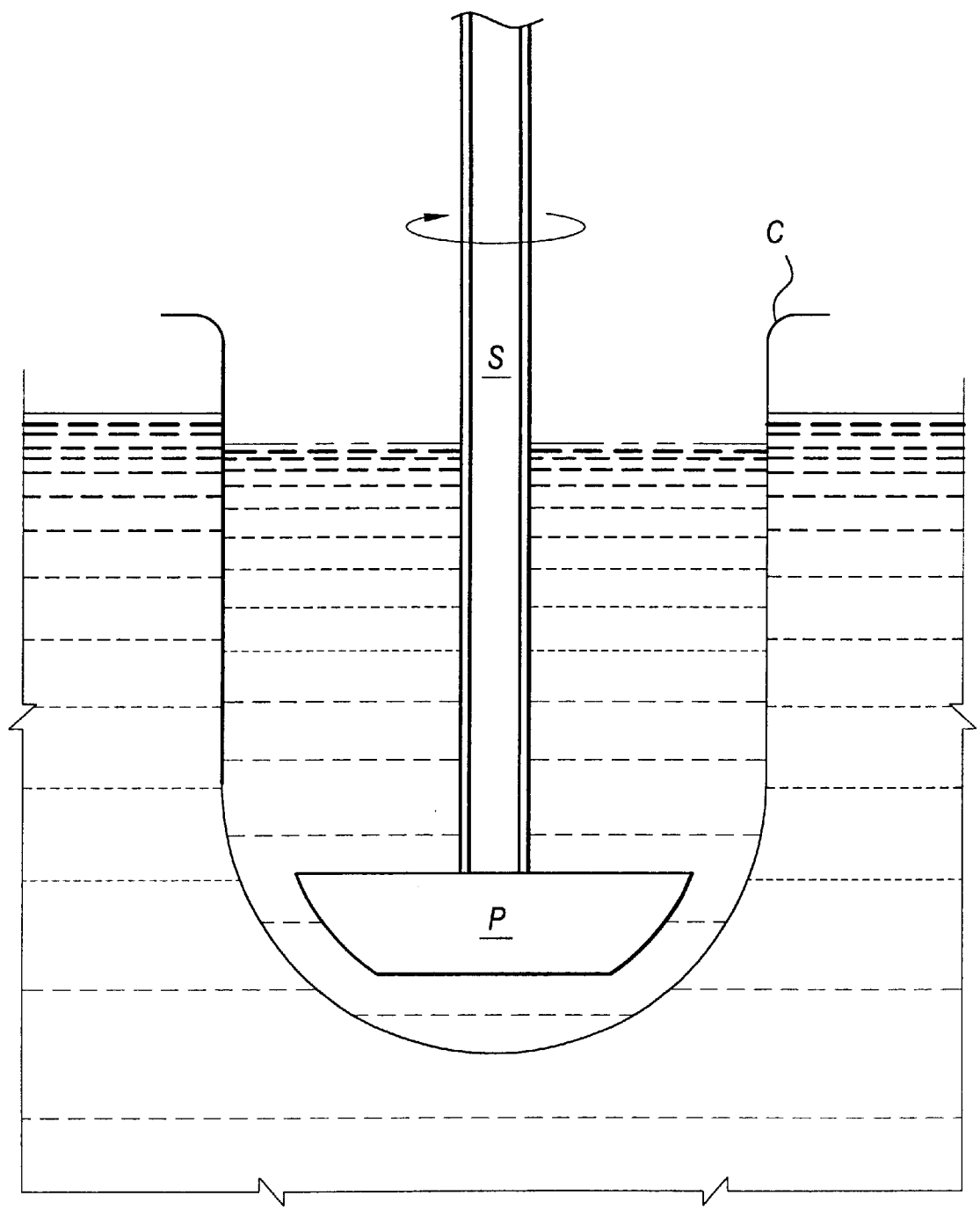
FIG. 2 is a diagrammatic, elevation view of a prior art dissolution tester.

Referring to FIG. 2, there is illustrated a prior art dissolution tester having a solution vessel C and an axial rotatable shaft s driving a paddle agitator P. The vessel is substantially submerged in a water bath held at 37° C.

Figure 3:
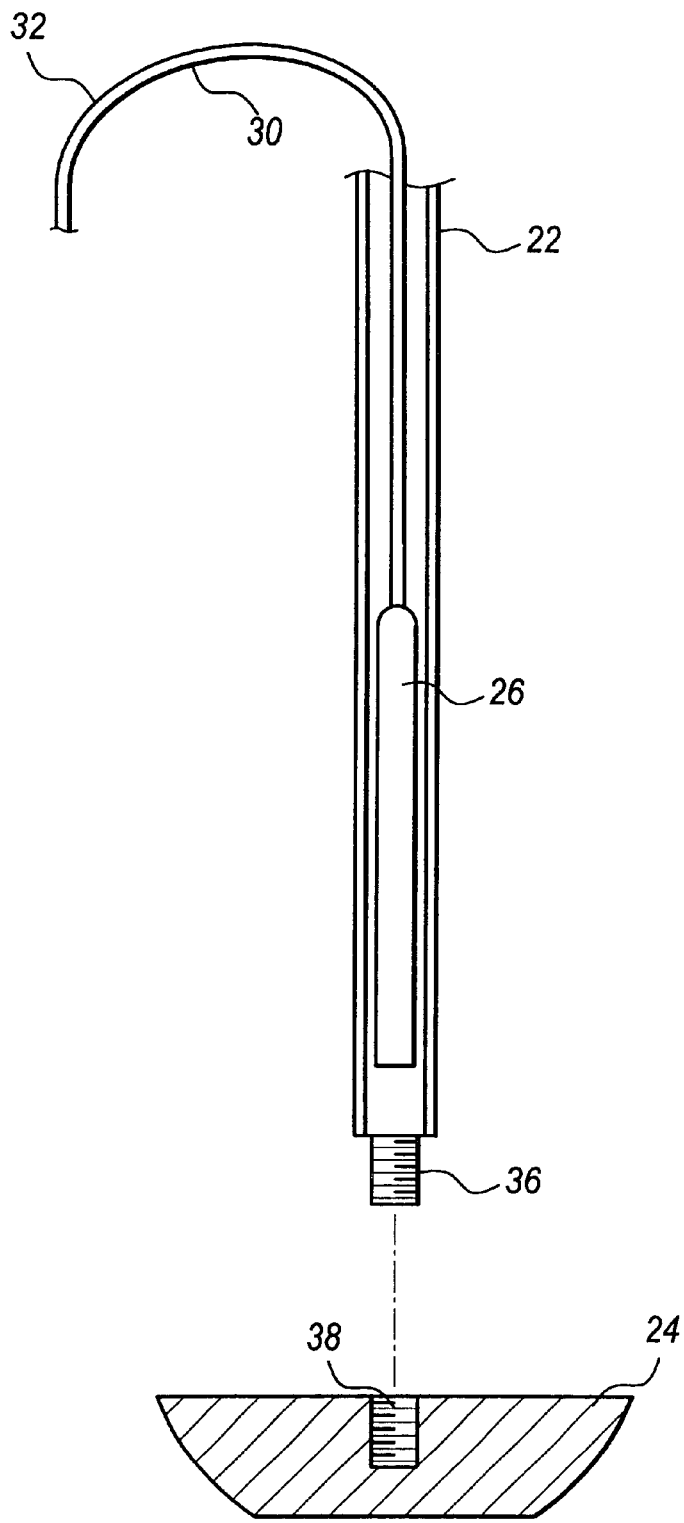
FIG. 3 is a diagrammatic exploded view of the heated shaft and paddle of the agitator of FIG. 1.

Referring to FIG. 3, there is illustrated an exploded view of the SS shaft 22 and two-bladed paddle agitator 24(shown in cross section). SS shaft 22 houses electrical heating element 26 connected with electrical conduits 30 and 32 as shown in FIG. 1. SS shaft 22 has a threaded end 36 which mates with centrally located threaded bore 38 in two-bladed paddle 24.

Figure 4:
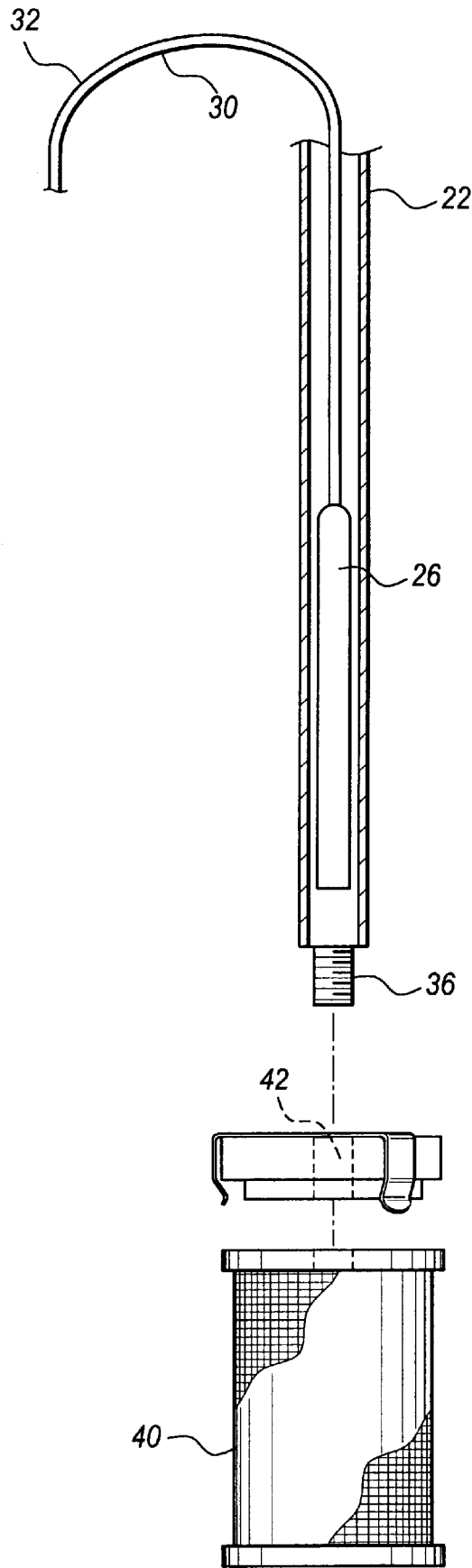
FIG. 4 is a diagrammatic exploded view of the heated shaft and basket, of an alternative agitator according to the present invention.

Referring to FIG. 4, there is illustrated an exploded view of an alternative embodiment of the present invention in which SS shaft 22 is identical to that of FIG. 3, but threaded end 36 mates with a basket-type agitator 40 by means of threaded bore 42.

In operation, test solution is added to dissolution vessel 16 suspended by air jacket 14, and electrical power is supplied to heating element 26 in rotating shaft 22, which drives agitator paddle 24, until the solution is brought up to temperature, i.e., 37° C. Warm air is directed upward into air jacket 14, surrounding test solution vessel 16. During this period, the test solution is degassed by the direct heat of the SS shaft and the agitation of agitator paddle 24. A tablet to be tested is dropped into the tester vessel and the time elapsed until complete dissolution of the tablet into the test solution is measured. The heat supplied to heating element 26 during the dissolution test is controlled by control 28 in a known manner in response to the temperature measured by temperature sensor 18 to maintain the solution at the required 37° C. temperature. Temperature data may be taken and recorded by the control as desired. The air jacket 14 and the tester solution vessel 16 are preferably made from a transparent material, such as glass, so the dissolution of the tablet may be observed. When employing the basket agitator of FIG. 4, the tablet is placed inside the basket and its dissolution observed. The basket is preferably made from wire mesh with metal fittings such as stainless steel.

It is to be understood that the present invention is not limited to the embodiments described above, but encompasses any and all embodiments within the scope of the following claims.

I claim:

1. An air bath dissolution tester meeting USP requirements comprising:
   a) a generally cylindrical test solution vessel having a cylindrical sidewall, a bottom portion and an upper opening lip;
   b) a warm air chamber substantially surrounding said sidewall and bottom portion of said test solution vessel;
   c) a stirring element having a rotatable vertical shaft having a hollow portion, and an agitator located at a lower end of said shaft, said shaft being substantially axially located within said test solution vessel; and
   d) a heating element located within said hollow portion of said vertical shaft.

2. The dissolution tester of claim 1, wherein said warm air chamber is in the form of a cylindrical jacket having an open upper end, and said upper opening lip of said test solution vessel rests upon said jacket upper end.

3. The dissolution tester of claim 1, wherein said heating element is and electrical heating element.

4. The dissolution tester of claim 3, further comprising a control, electrically connected with said heating element, and a temperature sensor for measuring the temperature of said test solution vessel and electrically connected with said control, said control being responsive to said temperature sensor so as to allow heating of said test solution to a desired test temperature and maintaining that temperature for the duration of a dissolution test.

5. The dissolution tester of claim 4, wherein said temperature sensor is attached to the exterior surface of said bottom portion of said test solution vessel and maintained in intimate contact therewith.

6. The dissolution tester of claim 5, wherein said agitator is a USP standard paddle.

7. The dissolution tester of claim 5, wherein said agitator is a USP standard basket.

8. The dissolution tester of claim 1 wherein said shaft lower end further comprises a threaded portion and said agitator comprises a centrally located threaded bore so configured as to threadingly engage said shaft threaded portion.

9. The dissolution tester of claim 1, wherein said test solution vessel and said warm air chamber are substantially transparent.

10. The dissolution tester of claim 9, wherein said test solution vessel and said warm air chamber are made of transparent glass.

11. The dissolution tester of claim 4, wherein said maintained temperature is about 37° C.

12. A dissolution tester meeting USP requirements comprising:
   a) a test solution vessel:
   b) means for stirring test solution in said vessel which meets USP requirements;
   c) means for heating said stirring means; and
   d) means for obtaining and maintaining said test solution vessel at a desired temperature.

13. The dissolution tester of claim 12, wherein said means for obtaining and maintaining said test solution vessel at a desired temperature comprises a warm air bath.

14. The dissolution tester of claim 13, wherein said means for obtaining and maintaining said test solution vessel at a desired temperature further comprises a heating element disposed within said stirring means.

15. The dissolution tester of claim 14, wherein said heating element is an electrical heating element.

16. The dissolution tester of claim 15, wherein said means for obtaining and maintaining said test solution vessel at a desired temperature further comprises a temperature sensor for measuring the temperature of said test solution vessel.

17. The dissolution tester of claim 16, wherein said means for obtaining and maintaining said test solution vessel at a desired temperature further comprises a controller, electrically connected with said heating element and said temperature sensor, said controller being responsive to said temperature sensor for controlling electrical power supplied to said electrical heating element.

18. The dissolution tester of claim 14, wherein said stirring means comprises a vertically oriented, rotatable shaft and an agitator located at a lower end of said shaft, said heating element being disposed within said rotatable shaft.

19. The dissolution tester of claim 18, wherein said agitator is a USP standard paddle.

20. The dissolution tester of claim 18, wherein said agitator is a USP standard basket.

* * * * *